(12) United States Patent
Schmidt et al.

(10) Patent No.: US 7,255,900 B2
(45) Date of Patent: Aug. 14, 2007

(54) FLUORINATED HETEROCYCLES AND THEIR USE IN LIQUID-CRYSTAL MIXTURES

(75) Inventors: Wolfgang Schmidt, Dreieich (DE); Rainer Wingen, Hofheim (DE); Barbara Hornung, Hasselroth (DE)

(73) Assignee: Merck Patent GmbH, Darmstadt (DE)

( * ) Notice: Subject to any disclaimer, the term of this patent is extended or adjusted under 35 U.S.C. 154(b) by 171 days.

(21) Appl. No.: 11/117,280

(22) Filed: Apr. 28, 2005

(65) Prior Publication Data
US 2005/0258399 A1    Nov. 24, 2005

(30) Foreign Application Priority Data
Apr. 30, 2004   (DE)   ................ 10 2004 021 691

(51) Int. Cl.
C09K 19/34   (2006.01)
C09K 19/32   (2006.01)
C09K 19/42   (2006.01)
C07D 307/91  (2006.01)
C07C 23/18   (2006.01)

(52) U.S. Cl. ............. 428/1.1; 252/299.61; 252/299.62; 549/458; 570/183; 570/187

(58) Field of Classification Search ................. 428/1.1; 252/299.61, 299.62, 299.01; 570/183; 549/458
See application file for complete search history.

(56) References Cited

U.S. PATENT DOCUMENTS

| | | |
|---|---|---|
| 5,648,021 A | 7/1997 | Wingen et al. |
| 5,888,422 A | 3/1999 | Manero et al. |
| 6,168,838 B1 | 1/2001 | Schmidt et al. |
| 6,558,758 B1 | 5/2003 | Yanai et al. |
| 7,018,685 B2 * | 3/2006 | Schmidt et al. ............... 428/1.1 |
| 7,067,179 B1 * | 6/2006 | Ogawa et al. ............... 428/1.1 |
| 7,087,272 B2 * | 8/2006 | Bremer et al. ............... 428/1.1 |
| 2004/0106798 A1 | 6/2004 | Bremer et al. |
| 2004/0124399 A1 | 7/2004 | Schmidt et al. |

FOREIGN PATENT DOCUMENTS

| | | |
|---|---|---|
| DE | 195 00 768 | 9/1995 |
| DE | 100 50 071 A 1 | 6/2001 |
| EP | 0 837 851 | 4/1998 |
| EP | 0 946 473 | 10/1999 |
| EP | 1 201 632 | 5/2002 |
| EP | 1 223 210 | 7/2002 |
| JP | 10-236992 | 9/1998 |
| WO | WO 01/10803 | 2/2001 |
| WO | WO 02/055463 A1 | 7/2002 |
| WO | WO 02/079344 | 10/2002 |

OTHER PUBLICATIONS

English language abstract of EP 1 223 210.
Ichinose et al., "High Optical Anisotropy and Small Rotational Viscosity LC Mixture for Field-Sequential Color TN-LCDs", IDW, LCT4-3, pp. 77-pp. 80 (2000).
Brown et al., "Aromatic Polyfluoro-Compounds-XXXVIII1,2,3,4-Tetrafluorodibenzofuran and Some Nucleophilic Replacement Reactions", Tetrahedron, vol. 23, pp. 4041-pp. 4045 (1967).
Machine English Translation of JP 10-236992 from the Japanese Patent Office.

* cited by examiner

*Primary Examiner*—Shean C. Wu
(74) *Attorney, Agent, or Firm*—Millen, White, Zelano & Branigan, P.C.

(57) ABSTRACT

In the compound of the formula (I),

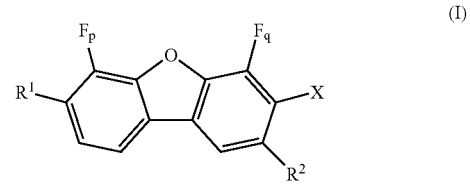

where:
$R^1$, $R^2$ are each independently, for example, H or a straight-chain or branched alkyl radical
p, q are each independently 0 or 1, i.e. at the value zero, —H is present at the appropriate position instead of —F
$M^1$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond
$A^1$ is, for example, 1,4-phenylene
$R^5$ has the same possible definitions as specified for $R^1$ and $R^2$, with the exception of —$M^1$—$A^1$—$R^5$, but independently of the definition of $R^1$ and $R^2$
X is H, F, OF$_3$, CF$_3$, OCF$_2$H
with the following provisos:
a) at least one of p, q has to be 1
b) $R^1$ and $R^2$ must not at the same time be H
c) $R^2$ and X must not at the same time be H.

20 Claims, 1 Drawing Sheet

τ-V$_{min}$ curve (T$_C$-30K; monopolar pulse; 1.3 μm)

FLUORINATED HETEROCYCLES AND THEIR USE IN LIQUID-CRYSTAL MIXTURES

This application claims priority to German Patent Application No. 10 2004 021 691.6, filed Apr. 30, 2004.

An ever-increasing number of applications of LCDs, for example for use in automobiles, in which a temperature range of from −40° C. to 100° C. can quite possibly exist, but also portable units such as cellphones and notebook PCs, requires liquid-crystal mixtures which have firstly a very wide working temperature range and secondly a minimum threshold voltage.

There is therefore a continuing demand for novel, suitable liquid-crystal mixtures and mixture components. As described in Ichinose et al. (IDW'00, Abstr. LCT4-3) or in DE-A 100 50 071, materials are being sought in which there is coexistence of high optical anisotropy (Δn) and low rotational viscosity, although other parameters such as high absolute values of dielectric anisotropy (Δε) are likewise preferentially required, in addition to further parameters relevant to the application.

Fluorinated dibenzofurans are known from WO 02/055463. In JP 10 236992, it is also possible to derive in a formal sense from the general formula specified there, among a multitude of other possibilities, a 3,7-disubstituted 1,2,8,9-tetrafluorodibenzofuran derivative, but the application does not consider the synthesis or physical properties of corresponding compounds.

1,2,3,4-Tetrafluorodibenzofuran and 1,2,4-trifluorodibenzofuran are known, for example, from Tetrahedron 1967, 23, 4041. However, suitability of these molecules or derivatives thereof as part of a component of liquid-crystal mixtures cannot be discerned therefrom.

Since the manufacturers of liquid-crystal displays have a constant interest in improved liquid-crystal mixtures, there is still a need for further components of liquid-crystal mixtures, with which individual parameters relevant to the application, for example the dielectric anisotropy (Δε) or the optical anisotropy (Δn), may be optimized.

It is therefore an object of the present invention to provide novel components for use in nematic or cholesteric or chiral-smectic liquid-crystal mixtures which have high absolute values of dielectric anisotropy combined with a favorable ratio of viscosity to clearing point. In addition, the compounds should to a high degree preferably be light- and UV-stable, and also thermally stable. In addition, they should preferably be suitable for realizing a high voltage holding ratio (VHR). In addition, they should have good synthetic accessibility and therefore potentially be inexpensive.

Figure 1:
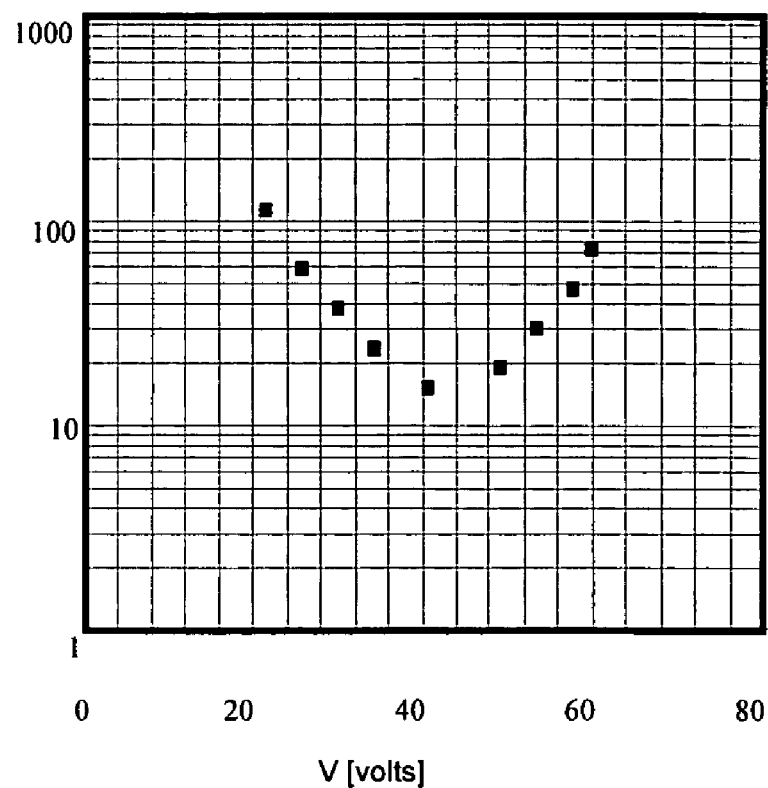
FIG. 1 shows the τVmin curve (τ~plotted against the voltage) at $T_c-30K$, monopolar pulses and a cell separation of 1.3 μm.

According to the invention, these objects are achieved by compounds of the formula (I)

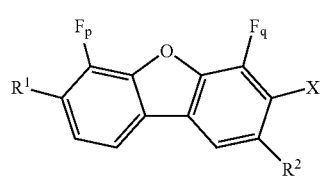

(I)

where:
$R^1$, $R^2$ are each independently a) H b) a straight-chain or branched alkyl radical having from 1 to 16 carbon atoms or a straight-chain or branched alkenyl radical having from 2 to 16 carbon atoms, in which b1) one or more nonadjacent and nonterminal $CH_2$ groups may be replaced by —O—, —C(=O)O—, —O—C(=O)—, —O—C(=O)—O—, —C(=O)— or —Si$(CH_3)_2$— and/or b2) one $CH_2$ group may be replaced by —C≡C—, cyclopropane-1,2-diyl, cyclobutane-1,3-diyl, cyclohexane-1,4-diyl or phenylene-1,4-diyl and/or b3) one or more hydrogen atoms may be replaced by F and/or Cl c) —$M^1$—$A^1$—$R^5$ p, q are each independently 0 or 1, i.e. at the value zero, —H is present at the appropriate position instead of —F $M^1$ is —CO—O—, —O—CO—, —$CH_2$—O—, —O—$CH_2$—, —$CF_2$—O—, —O—$CF_2$—, —CH=CH—, —CF=CF—, —C≡C—, —$CH_2$—$CH_2$—CO—O—, —O—CO—$CH_2$—$CH_2$—, —$CH_2$—$CH_2$—, —$CF_2$—$CF_2$—, —$(CH_2)_4$—, —OC(=O)CF=CF— or a single bond $A^1$ is 1,4-phenylene in which one or two hydrogen atoms may be replaced by F, Cl, CN and/or $OCF_3$ or three hydrogen atoms may be replaced by fluorine, 1,4-cyclohexylene in which one or two hydrogen atoms may be replaced by $CH_3$ and/or F, 1-cyclohexene-1,4-diyl in which one hydrogen atom may be replaced by $CH_3$ or F, pyrimidine-2,5-diyl, pyridine-2,5-diyl or 1,3-dioxane-2,5-diyl $R^5$ has the same possible definitions as specified for $R^1$ and $R^2$, with the exception of —$M^1$—$A^1$—$R^5$, but independently of the definition of $R^1$ and $R^2$ X is H, F, $OCF_3$, $CF_3$, $OCF_2H$ with the following provisos:
a) at least one of p, q has to be 1
b) $R^1$ and $R^2$ must not at the same time be H
c) $R^2$ and X must not at the same time be H, and by liquid-crystal mixtures comprising these compounds.

Preference is given to compounds of the formulae (Ia) to (Id)

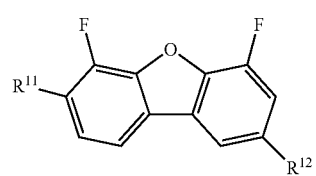

(Ia)

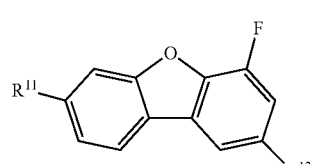

(Ib)

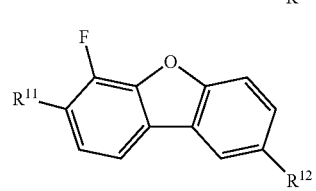

(Ic)

-continued

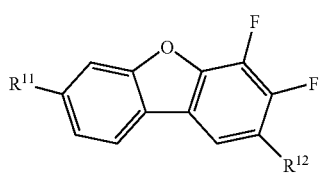
(Id)

in which:

R$^{11}$ and R$^{12}$ are each independently an alkyl or alkyloxy radical having from 1 to 10 carbon atoms or an alkenyl or alkenyloxy radical having from 2 to 10 carbon atoms, in which in each case one or more hydrogen atoms may also be replaced by F, or the R$^{15}$—A$^{15}$—M$^{15}$—moiety, with the proviso that:

R$^{11}$ and R$^{12}$ must not at the same time be R$^{15}$—A$^{15}$—M$^{15}$,

R$^{15}$ is an alkyl or alkyloxy radical having from 1 to 10 carbon atoms or an alkenyl or alkenyloxy radical having from 2 to 10 carbon atoms A$^{15}$ is phenylene-1,4-diyl, cyclohexane-1,4-diyl M$^{15}$ is a single bond, —CO—O—, —O—CO—, —C≡C—, —OCF$_2$—, —CF$_2$O—, —CF$_2$CF$_2$—, —CH$_2$CH$_2$—.

Particular preference, especially for use in nematic mixtures, is given to the compounds of the formulae (Ia1), (Ia2) and (Ia3)

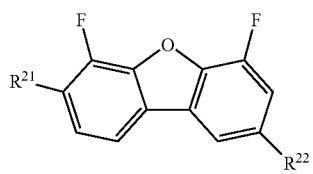
(Ia1)

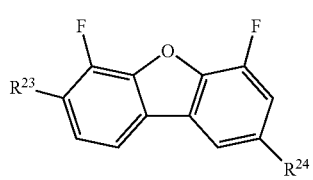
(Ia2)

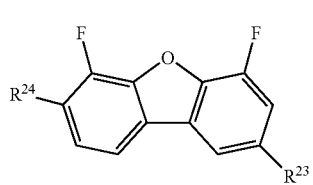
(Ia3)

in which:

R$^{21}$ and R$^{22}$ are each independently an alkyl or alkoxy radical having from 1 to 6 carbon atoms or an alkenyl or alkenyloxy radical having from 2 to 5 carbon atoms, R$^{23}$ is an alkyl or alkyloxy radical having from 1 to 6 carbon atoms or an alkenyl or alkenyloxy radical having from 2 to 5 carbon atoms, R$^{24}$ is the R$^{15}$—A$^{15}$—M$^{15}$— moiety in which R$^{15}$ is an alkyl or alkyloxy radical having from 1 to 10 carbon atoms or an alkenyl or alkenyloxy radical having from 2 to 10 carbon atoms A$^{15}$ is phenylene-1,4-diyl, cyclohexane-1,4-diyl M$^{15}$ is a single bond or —CH$_2$CH$_2$—.

The provision of compounds of the formula (I) in a quite general sense considerably broadens the range of liquid-crystalline substances which are suitable for producing liquid-crystalline mixtures from different performance aspects.

In this context, the compounds of the formula (I) have a broad field of application. Depending on the selection of the substituents, they may be added to other classes of compound, in order, for example, to influence the dielectric and/or optical anisotropy of such a dielectric. They may also serve to optimize its threshold voltage and/or its viscosity. The compounds may also serve to increase the mesophase range or to adjust individual mesophases to parameters relevant to the application.

The compounds of the formula (I) are particularly suitable, even in small amounts in the mixture, for influencing the dielectric anisotropy (Δε) and/or the optical anisotropy Δn of liquid-crystal mixtures. The compounds of the formula (I) are particularly suitable, even in small amounts in the mixture, for reducing the response time of ferroelectric liquid-crystal mixtures. The compounds of the formula (I) are likewise particularly suitable for adjusting the broadness of the S$_C$ or N phase to application requirements.

The present invention thus provides compounds of the formula (I) and for the use of these compounds as components of liquid-crystalline mixtures and liquid-crystal mixtures comprising one or more compounds of the formula (I).

The compounds of the formula (I) may be used in various liquid-crystal mixtures, for example chiral-smectic, nematic or cholesteric liquid-crystal mixtures. In the case of nematic mixtures, they are particularly suitable for active matrix displays (AM-LCD) (see, for example, C. Prince, Seminar Lecture Notes, Volume I, p. M-3/3-M-22, SID International Symposium 1997, B. B. Bahadur, Liquid Crystal Applications and Uses, Vol. 1, p. 410, World Scientific Publishing, 1990, E. Lüder, Recent Progress of AMLCD's, Proceedings of the 15$^{th}$ International Display Research Conference, 1995, p. 9–12) and in-plane-switching displays (IPS-LCD), and, in the case of smectic liquid-crystal mixtures, for smectic (ferroelectric or antiferroelectric) displays. Further display possibilities are the ECB and VA display mode in the case of nematic and cholesteric LC mixtures.

Further components of liquid-crystal mixtures which comprise inventive compounds of the formula (I) are preferably selected from the known compounds having smectic and/or nematic and/or cholesteric phases. Mixture components suitable in this context are listed in particular in WO 00/36054, DE-A-195 31 165 and EP-A-0 893 424, which are explicitly incorporated herein by way of reference.

The present invention also provides liquid-crystal mixtures, which comprise at least one compound of the formula (I), preferably in an amount of from 1 to 40% by weight, based on the liquid-crystal mixture. The mixtures preferably comprise at least 3 further components having smectic and/or nematic and/or cholesteric phases in addition to compounds of the formula (I). The invention additionally provides electrooptical displays (liquid-crystal displays) which comprise the inventive mixtures.

Preference is given to displays which comprise the inventive nematic or smectic (ferroelectric or antiferroelectric) mixtures in combination with active matrix elements.

The inventive displays are typically constructed in such a way that one liquid-crystal layer is enclosed on both sides by layers which are typically, in this sequence starting from the LC layer, at least one alignment layer, electrodes and a boundary layer (for example glass). In addition, they may comprise spacers, adhesive frames, polarizers and thin color filter layers for color displays. Further possible components are antireflection, passivation, compensation and barrier layers, and also electrically nonlinear elements such as thin-film transistors (TFT) and metal-insulator-metal (MIM) elements. The construction of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

An example of a possible synthetic route to compounds of the formula (I) is specified in scheme 1 which follows, although other processes are also feasible and possible.

The following abbreviations are used:
n-BuLi n-butyllithium
DCM dichloromethane
DME dimethoxyethane
DMF N,N-dimethylformamide
DMSO dimethyl sulfoxide
KOtBu potassium tert-butoxide
LICOR lithium organyl+potassium tert-butoxide
LiTMP lithium 2,2,6,6-tetramethylpiperidide
MEK methyl ethyl ketone (2-butanone)
MTBE tert-butyl methyl ether
4-TsOH 4-toluenesulfonic acid Scheme 1

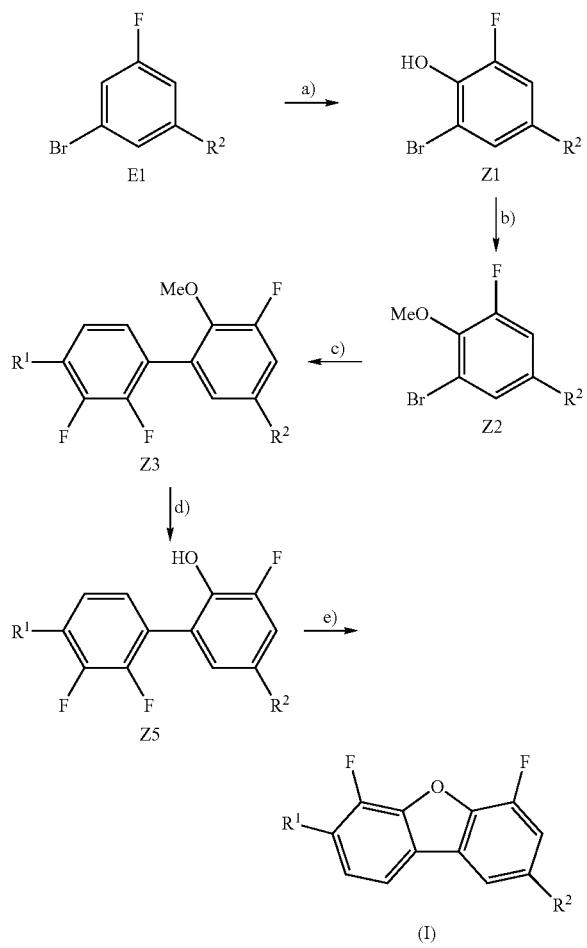

a) 1. LITMP according to *Tetrahedron Lett.* 1996, 37, 6551
  2. B(OMe)$_3$ 3. H$_3$O$^+$ 4. H$_2$O$_2$ according to *J. Chem. Soc., Perkin Trans. II* 1989, 2041
b) dimethyl sulfate, K$_2$CO$_3$, acetone
c) R$^1$-2,3-difluorophenylboronic acid, Pd$^0$ catalyst according to *J. Chem. Soc., Perkin Trans.* 2 1999, 481; *J. Chem. Soc., Perkin Trans.* 2, 2000, 27; *J. Am. Chem. Soc.* 2000, 122, 4020; *Tetrahedron Lett.* 2001, 42, 6523
d) BBr$_3$, DCM or HBr, AcOH or Ph2PLi, THF according to *Synthesis* 1983, 249; *J. Mater. Chem.* 2002, 12, 1316; *Liq. Cryst* 1998, 25, 1; *Liq. Cryst* 1998, 25, 47; *Synthesis* 1978, 771.
e) K$_2$CO$_3$/DMF according to *New. J. Chem* 2001, 25, 385; *Synthesis* 1998, 894.

The reactant E1 where R$^2$=methyl is known from the literature [202865-83-6] and commercially available; reactants E1 where R$^2$=alkyl can be prepared from the compound E1 where R$^2$=CHO [188813-02-7] which is known from the literature by Wittig reaction with alkyltriphenylphosphonium halides and subsequent hydrogenation; alternatively, the commercially available compound where R$^2$=CN [179898-34-1] may be reacted with alkylmagnesium halides and subsequently processed reductively to give the target compounds. Reactants where R$^2$=OMe [29578-39-0] and OEt [212307-87-4] are known from the literature; higher homologs may be obtained, for example, from 3-bromo-5-fluorophenol (E1 where R$^2$=OH) [433939-27-6] by etherification with alkyl bromides.

The further starting materials (for example R$^1$-2,3-difluorophenylboronic acids) are familiar to those skilled in the art (for example: J. Chem. Soc., Perkin Trans. 2 1999, 481; J. Chem. Soc., Perkin Trans. 2, 2000, 27) and some are even commercially available.

The invention is illustrated in detail by the examples which follow.

EXAMPLE 1

4,6-Difluoro-2,7-dipropyldibenzofuran

[Compound (I) where p=q=1, X=H, R$^1$=C$_3$H$_7$, R$^2$=C$_3$H$_7$]

Under protective gas, 10.7 g of 2,3-difluoro-4-propylphenylboronic acid (prepared from 1,2-difluoro-3-propylbenzene by lithiation with n-BuLi in THF at −70° C. and subsequent reaction with trimethyl borate according to J. Chem. Soc., Perkin Trans. II 1989, 2041), 8.9 g of anhydrous potassium fluoride and 0.64 g of tris(dibenzylideneacetone)dipalladium(0) are initially charged, and admixed successively with a solution of 11.5 g of 2-bromo-6-fluoro-4-propylanisole (prepared by etherification of 2-bromo-6-fluoro-4-propylphenol with dimethyl sulfate and potassium carbonate in acetone; 2-bromo-6-fluoro-4-propylphenol was obtained by lithiation of 1-bromo-5-fluoro-3-propylbenzene with LITMP in THF at −70° C. and subsequent reaction with trimethyl borate, acidic workup and oxidation with H$_2$O$_2$ in MTBE according to Tetrahedron Lett. 1996, 37, 6551 and J. Chem. Soc., Perkin Trans. II 1989, 2041; 1-bromo-5-fluoro-3-propylbenzene was obtained from 3-bromo-5-fluorobenzaldehyde [188813-02-7 by Wittig reaction with ethyltriphenylphosphonium bromide and subsequent cat. hydrogenation) in 90 ml of dry 1,4-dioxane and 0.38 g of tri-tert-butylphosphine (dissolved in approx. 5 ml of the same solvent). The mixture is heated to boiling under vigorous stirring for 6 h. After cooling, the reaction mixture is added to water and extracted with MTBE. The org. phase is removed, washed with water and sat. sodium chloride solution, and dried over sodium sulfate, and the solvents are removed under reduced pressure. The crude product is purified by chromatography on silica gel with heptane/dichloromethane (8:2 v/v) as the eluent. The thus obtained 3,2',3'-trifluoro-2-methoxy-5,4'-dipropylbiphenyl is heated to boiling in a mixture of 75 ml of glacial acetic acid and 65 ml of 48% aqueous hydrobromic acid overnight. After cooling, the reaction mixture is added to ice-water and extracted with ethyl acetate. The combined organic phases are washed with water and 5% sodium hydrogencarbonate solution and dried over sodium sulfate. After the solvent has been removed under reduced pressure, the black-brown residue is purified chromatographically on silica gel using 7:3 heptane/dichloromethane as the eluent. The resulting 3,2',3'-trifluoro-5,4'-dipropylbiphenyl-2-ol is heated to 90–100° C. with 8.2 g of potassium carbonate in 270 ml of dimethylformamide for 6 h. After cooling, the reaction mixture is added to approx. 1 l of water and extracted twice with dichloromethane, and the organic phases are combined, washed twice with saturated sodium chloride solution and subsequently twice with water and dried over sodium sulfate. The brown residue which is obtained after the solvent has been distilled off is chromatographed using silica gel with toluene as the eluent. After the solvent has been removed under reduced pressure, the product-containing fractions are recrystallized from heptane. 3.2 g of 4,6-difluoro-2,7-dipropyldibenzofuran are obtained.

EXAMPLE 2

2-Butyl-4,6-difluoro-7-propyldibenzofuran

[Compound (I) where p=q=1, X=H, $R^1$=$C_3H_7$, $R^2$=$C_4H_9$]

Analogously to example 1, using 2-bromo-4-butyl-6-fluoroanisole instead of 2-bromo-6-fluoro-4-propylanisole, 2-butyl-4,6-difluoro-7-propyldibenzofuran is obtained.

EXAMPLE 3

7-Butyloxy-4,6-difluoro-2-propyldibenzofuran

[Compound (I) where p=q=1, X=H, $R^1$=$OC_4H_9$, $R^2$=$C_3H_7$]

Analogously to example 1, using 4-butyloxy-2,3-difluorophenylboronic acid (prepared from 1-butyloxy-2,3-difluorobenzene by lithiation with n-BuLi in THF at −70° C. and subsequent reaction with trimethyl borate according to J. Chem. Soc., Perkin Trans. II 1989, 2041) instead of 2,3-difluoro-4-propylphenylboronic acid, 7-butyloxy4,6-difluoro-2-propyldibenzofuran is obtained.

USE EXAMPLE 1

A chiral-smectic C mixture consisting of

| | |
|---|---|
| 2-(4-heptyloxyphenyl)-5-nonylpyrimidine | 19.6% |
| 5-nonyl-2-(4-octyloxyphenyl)pyrimidine | 19.6% |
| 5-nonyl-2-(4-nonyloxyphenyl)pyrimidine | 19.6% |
| 2-(2,3-difluoro-4-heptyloxyphenyl)-5-nonylpyrimidine | 6.5% |
| 2-(2,3-difluoro-4-octyloxyphenyl)-5-nonylpyrimidine | 6.5% |
| 2-(2,3-difluoro-4-nonyloxyphenyl)-5-nonylpyrimidine | 6.5% |
| 5-hexyloxy-2-(4-hexyloxyphenyl)pyrimidine | 19.6% |
| (S)-4-[4'-(2-fluorooctyloxy)biphenyl-4-yl]-1-heptylcyclohexanecarbonitrile | 2.0% | is admixed with 5% of the compound from example 1. This results in a mixture which, as demonstrated by FIG. 1, is suitable for the operation of displays in inverse mode, since the curve profile has the required minimum and the values lie within the technically relevant range.

What is claimed is:

1. A compound of formula (I),

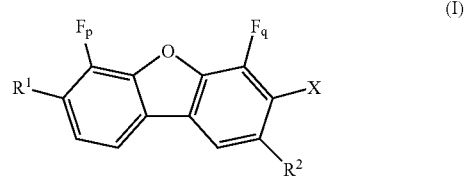

wherein $R^1$ and $R^2$ are, each independently, a) H b) a straight-chain or branched alkyl radical having 1 to 16 carbon atoms, or a straight-chain or branched alkenyl radical having 2 to 16 carbon atoms, in which b1) one or more nonadjacent and nonterminal $CH_2$ groups may be replaced by —O—, —C(=O)O—, —O—C(=O)—, —O—C(=O)—O—, —C(=O)— or —Si(CH$_3$)$_2$— and/or b2) one $CH_2$ group may be replaced by —C≡C—, cyclopropane-1,2-diyl, cyclobutane-1,3-diyl, cyclohexane-1,4-diyl or phenylene-1,4-diyl and/or b3) one or more hydrogen atoms may be replaced by F and/or Cl, c) —$M^1$—$A^1$—$R^5$, p, q are, each independently, 0 or 1, and in case p or q is zero, —H is present instead of —F, $M^1$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond, $A^1$ is 1,4-phenylene in which one or two hydrogen atoms may be replaced by F, Cl, CN and/or OCF$_3$, or three hydrogen atoms may be replaced by fluorine, 1,4-cyclohexylene in which one or two hydrogen atoms may be replaced by CH$_3$ and/or F, 1-cyclohexene-1,4-diyl in which one hydrogen atom may be replaced by CH$_3$ or F, pyrimidine-2,5-diyl, pyridine-2,5-diyl or 1,3-dioxane-2,5-diyl $R^5$ has the same definition as specified for $R^1$ and $R^2$, with the exception of —$M^1$—$A^1$—$R^5$, but independently of the definition of $R^1$ and $R^2$, X is H, F, OCF$_3$, CF$_3$, or OCF$_2$H, with the following provisos:

a) at least one of p, q has to be 1, b) $R^1$ and $R^2$ must not at the same time be H, c) $R^2$ and X must not at the same time be H.

2. A compound according to claim 1, which is of formula (Ia1), (Ia2) or (Ia3)

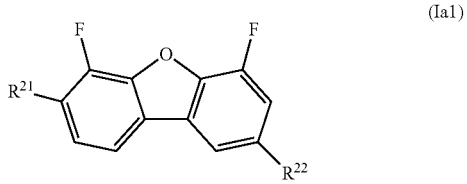

-continued

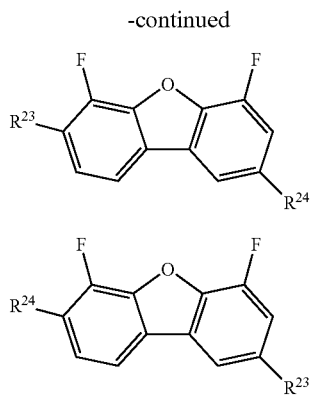

in which:
R²¹ and R²² are, each independently, an alkyl or alkoxy radical having 1 to 6 carbon atoms, or an alkenyl or alkenyloxy radical having 2 to 5 carbon atoms,
R²³ is an alkyl or alkyloxy radical having 1 to 6 carbon atoms, or an alkenyl or alkenyloxy radical having 2 to 5 carbon atoms,
R²⁴ is R¹⁵—A¹⁵—M¹⁵,
R¹⁵ is an alkyl or alkyloxy radical having 1 to 10 carbon atoms, or an alkenyl or alkenyloxy radical having 2 to 10 carbon atoms,
A¹⁵ is phenylene-1,4-diyl, or cyclohexane-1,4-diyl, and
M¹⁵ is a single bond or —CH₂CH₂—.

3. A liquid-crystal mixture which comprises one or more compounds of formula (I) according to claim 1.

4. A liquid-crystal mixture according to claim 3, which comprises one or more compounds of formula (I) in an amount of 1 to 40% by weight, based on the liquid-crystal mixture.

5. A liquid-crystal mixture according to claim 3, which comprises at least three further components having smectic and/or nematic and/or cholesteric phases.

6. A liquid-crystal mixture according to claim 3, which is chiral-smectic.

7. A liquid-crystal mixture according to claim 3, which is nematic or cholesteric.

8. A liquid-crystal display comprising a liquid-crystal mixture according to claim 3.

9. A liquid-crystal display according to claim 8 which is operated in ECB, IPS or VA display mode and comprises a nematic or cholesteric liquid-crystal mixture.

10. A compound according to claim 1, which is of formula (Ia), (Ib), (Ic) or (Id)

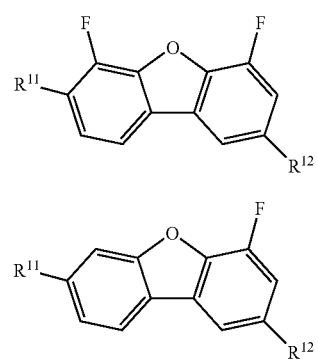

-continued

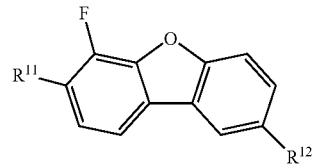

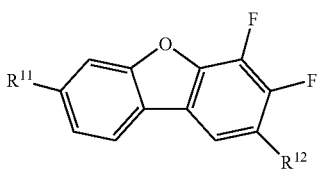

in which:
R¹¹ and R¹² are, each independently, an alkyl or alkyloxy radical having 1 to 10 carbon atoms, or an alkenyl or alkenyloxy radical having 2 to 10 carbon atoms, in which in each case one or more hydrogen atoms may be replaced by F, or R¹⁵—A¹⁵—M¹⁵,
with the proviso that:
R¹¹ and R¹² are not at the same time R¹⁵—A¹⁵—M¹⁵,
R¹⁵ is an alkyl or alkyloxy radical having 1 to 10 carbon atoms or an alkenyl, or alkenyloxy radical having 2 to 10 carbon atoms,
A¹⁵ is phenylene-1,4-diyl, or cyclohexane-1,4-diyl, and
M¹⁵ is a single bond, —CO—O—, —O—CO—, —C═C—, —OCF₂—, —CF₂O—, —CF₂CF₂—, or —CH₂CH₂—.

11. A compound according to claim 1, which is 4,6-Difluoro-2,7-dipropyldibenzofuran, 2-Butyl-4,6-difluoro-7-propyldibenzofuran, or 7-Butyloxy-4,6-difluoro-2-propyldibenzofuran.

12. A compound according to claim 10, which is a compound of formula (Ia).

13. A liquid-crystal mixture which comprises one or more compounds of formula (Ia1), (Ia2) or (Ia3) according to claim 2.

14. A liquid-crystal mixture which comprises one or more compounds of formula (Ia), (Ib), (Ic) or (Id) according to claim 10.

15. A liquid-crystal mixture which comprises one or more compounds of formula (Ia) according to claim 10.

16. A liquid-crystal display comprising a liquid-crystal mixture according to claim 13.

17. A liquid-crystal display comprising a liquid-crystal mixture according to claim 14.

18. A liquid-crystal display comprising a liquid-crystal mixture according to claim 15.

19. A liquid-crystal display according to claim 16 which is operated in ECB, IPS or VA display mode and comprises a nematic or cholesteric liquid-crystal mixture.

20. A liquid-crystal display according to claim 18 which is operated in ECB, IPS or VA display mode and comprises a nematic or cholesteric liquid-crystal mixture.

* * * * *

UNITED STATES PATENT AND TRADEMARK OFFICE
CERTIFICATE OF CORRECTION

PATENT NO. : 7,255,900 B2 Page 1 of 1
APPLICATION NO. : 11/117280
DATED : August 14, 2007
INVENTOR(S) : Wolfgang Schmidt It is certified that error appears in the above-identified patent and that said Letters Patent is hereby corrected as shown below:

Column 10, line 24, reads "F,or" should read -- F, or --
Column 10, line 34, reads "-C=C-" should read -- -C≡C-, --

Signed and Sealed this

Fourth Day of March, 2008

JON W. DUDAS
*Director of the United States Patent and Trademark Office*